United States Patent [19]

Chang

[11] Patent Number: 4,830,659
[45] Date of Patent: May 16, 1989

[54] 9-(2H-1,4-BENZOXAZIN-3(4H)-ON-6-YL)IMINO-8-THIA-1,6-DIAZOBICY-CLO[4.3.0]NONANE-7-ONE(AND THIONES)HERBICIDES

[75] Inventor: Jun H. Chang, Princeton Junction, N.J.

[73] Assignee: FMC Corporation, Philadelphia, Pa.

[21] Appl. No.: 211,640

[22] Filed: Jun. 27, 1988

[51] Int. Cl.$^4$ .................. A01N 43/90; C07D 513/04
[52] U.S. Cl. ........................................ 71/90; 544/105
[58] Field of Search .............................. 544/105; 71/90

[56] References Cited

U.S. PATENT DOCUMENTS

| 4,619,687 | 10/1986 | Haga et al. | 71/92 |
| 4,755,217 | 7/1988 | Chang et al. | 71/84 |

FOREIGN PATENT DOCUMENTS 0170191  2/1986  European Pat. Off.
62-91    3/1986  Japan.

OTHER PUBLICATIONS

Abstract (Derwent) 87-0407 49/06 of Japan 62-91 (above).

Primary Examiner—Richard L. Raymond
Attorney, Agent, or Firm—Robert M. Kennedy; H. Robinson Ertelt; Robert L. Andersen

[57] ABSTRACT

Disclosed are herbicidal compounds, compositions containing the herbicidal compounds, and a method for controlling undesired plant growth by application of the herbicidal compositions. The herbicidal compounds are compounds of the formula

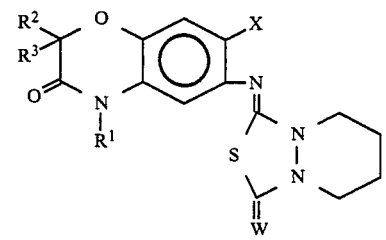

in which $R^1$ is hydrogen, alkyl, alkenyl, alkynyl, haloalkyl, haloalkenyl, haloalkynyl, alkoxyalkyl, alkoxyalkoxyalkyl, cycloalkyl, aralkyl, alkylthioalkyl, hydroxy, or alkoxy; $R^2$ and $R^3$ are independently hydrogen or alkyl; X is hydrogen, chlorine, bromine, or fluorine; and W is oxygen or sulfur.

7 Claims, No Drawings

9-(2H-1,4-BENZOXAZIN-3(4H)-ON-6-YL)IMINO-8-THIA-1,6-DIAZOBICYCLO[4.3.0]NONANE-7-ONE-(AND THIONES)HERBICIDES

This invention relates to compounds of the following formula and their use as herbicides:

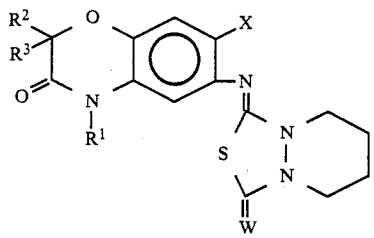

Formula I in which $R^1$ is:
H;
alkyl, e.g. methyl, ethyl or propyl;
alkenyl, e.g. allyl or methylallyl;
alkynyl, e.g. propynyl or methylpropynyl;
haloalkyl, e.g. 3-chloropropyl;
haloalkenyl, e.g. 2-chloroallyl or 2,3-dichloro-allyl;
haloalkynyl, e.g. 3-bromopropynyl;
alkoxyalkyl, e.g. methoxymethyl or ethoxymethyl;
alkoxyalkoxyalkyl, e.g. ethoxymethoxymethyl;
cycloalkyl, e.g. cyclopropylmethyl or cyclopropyl;
aralkyl, e.g. benzyl;
alkylthioalkyl, e.g. methylthiomethyl; hydroxy; or
alkoxy, e.g. methoxy or ethoxy.
$R^2$ and $R^3$ are, independently, H or alkyl, e.g. methyl, preferably H.
X is H, Cl, Br or F, preferably F.
W is S or O.

In each aspect of the invention it is often preferable that any alkyl, alkenyl, alkynyl or alkylene moiety (such as the hydrocarbon moiety of an alkoxy or halo-alkoxy group) have less than 6 carbon atoms, e.g. 1 to 3 carbon atoms.

The compounds of this invention may be prepared by the use of steps generally described in the literature or in the following examples or by methods analogous or similar thereto and within the skill of the art. In Example 1 below, the product is produced by reacting a compound of the formula:

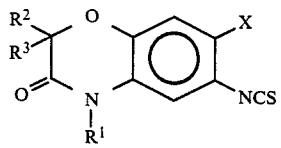

Formula II such as a compound of formula IV of U.S. Pat. No. 4,619,687, with perhydropyridazine (e.g. in the form of its hydroiodide salt) to form a compound of the formula

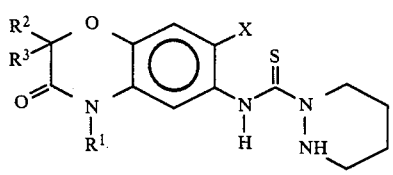

Formula III followed by reaction with thiophosgene (or phosgene) to form the final product of Formula I.

The following examples are given to illustrate the invention further. Proportions are by weight and temperatures are centigrade unless otherwise specified.

EXAMPLE 1

9-(7-Fluoro-4-propyl-2H-1,4-benzoxazin-3(4H)-on-6-yl)imino-8-thia-1,6-diazabicyclo-[4.3.0]nonane-7-thione Step A:
N-(7-fluoro-4-propyl-2H-1,4-benzoxazin-3(4H)-on-6-yl)aminothiocarbonylperhydropyridazine To a stirred, cold ($-20°$ C.) solution of 11.3 g (0.0529 mole) of perhydropyridazine hydroiodide in 200 mL of methylene chloride was added 16.1 g (0.159 mole) of triethylamine. While maintaining a reaction temperature of $-25°$ C., a solution of 12.8 g (0.0481 mole) of (7-fluoro-4-propyl-2H-1,4-benzoxazin-3(4H)-on-6-yl)isothio-cyanate in methylene chloride was added. After complete addition, the reaction mixture was stirred at $-20°$ C. for 2.5 hours. The solvent was removed from the mixture by evaporation under reduced pressure leaving a residue. This residue was partitioned between ethyl acetate and water. The organic phase was dried over anhydrous magnesium sulfate and was filtered. The filtrate was evaporated under reduced pressure leaving an oily solid residue. This oily solid was dissolved in methylene chloride to which was added n-heptane, causing a precipitate to form. The precipitate was collected by filtration and was dried to yield 12.0 g of N-(7-fluoro-4-propyl-2H-1,4-benzoxazin-3(4H)-on-6yl)aminothiocar-bonylperhydropyridazine.

The nmr spectrum was consistent with the proposed structure.

Step B:
9-(7-Fluoro-4-propyl-2H-1,4-benzoxazin-3(4H)-on-6-yl)imino-8-thia-1,6-diazabicyclo-[4.3.0]nonane-7-thione To a stirred, cold ($-20°$) solution of 12.0 g (0.0340 mole) of N-(7-fluoro-4-propyl-2H-1,4-benzoxazin-3(4H)-on-6-yl)aminothiocarbonylperhydropyridazine and 8.69 g (0.110 mole) of pyridine in 300 mL of methylene chloride was added dropwise 3.90 g (0.0340 mole) of thiophosgene. The resulting mixture was stirred at room temperature for approximately 18 hours. The reaction mixture was washed with dilute hydrochloric acid followed by an aqueous, saturated sodium chloride solution. The washed organic phase was dried over anhydrous magnesium sulfate and was filtered. The filtrate was treated with decolorizing charcoal and was filtered through a pad of silica gel. The filtrate was evaporated under reduced pressure leaving a solid residue. This residue (10.4 g) was combined with 3.6 g of a similar residue prepared in a similar manner. The resultant solid (14.0 g) was recrystallized from ethyl acetate and n-heptane to yield 11.7 g of 9-(7-fluoro-4-propyl-2H-1,4-benzoxazin-3(4H)-on-6-yl)imino-8-thia-1,6-diazabicyclo[4.3.0]nonane-7-thione, mp 112°–114° C. (corresponding to Compound 5 of Table 1).

The ir and nmr spectra were consistent with the proposed structure.

Analysis Calcd for $C_{17}H_{19}FN_4O_2S_2$: C51.76; H4.85; N14.20. Found: C51.56; H4.80; N13.94.

EXAMPLE 2

[7-Fluoro-4-(2-propynyl)-2H-1,4-benzoxazin-3(4H)-on-6-yl]isothiocyanate was converted into 9-[7- fluoro-4-(2-propynyl)-2H-1,4-benzoxazin-3(4H)-on-6-yl]imino-8-thia-1,6-diazabicyclo[4.3.0]nonane-7-thione (Compound 6 of Table 1) was prepared by the general method of Example 1, mp 205°–206° C.

The ir and nmr spectra were consistent for the proposed structures.

The following results were obtained in preemergence and postemergence testing for herbicidal activity by the procedure described below.

| Application Rate: | Percent Control | | | |
|---|---|---|---|---|
| | Compound 5 0.25 kg/ha | | Compound 6 0.0625 kg/ha | |
| Species | Pre | Post | Pre | Post |
| Cotton | 60 | 100 | 10 | 100 |
| Soybean | 60 | 80 | 5 | 90 |
| Corn | 40 | 90 | 5 | 50 |
| Rice | 50 | 90 | 20 | 60 |
| Wheat | 40 | 80 | 0 | 60 |
| Morningglory | 100 | 100 | 70 | 100 |
| Wild Mustard | 90 | 100 | 95 | 100 |
| Velvetleaf | 100 | 100 | 100 | 100 |
| Barnyardgrass | 40 | 50 | 40 | 50 |
| Green Foxtail | 20 | 95 | 40 | 85 |
| Johnsongrass | 70 | 50 | 40 | 80 |

HERBICIDAL ACTIVITY

The plant test species used in demonstrating the herbicidal activity of compounds of this invention include cotton (*Gossypium hirsutum* var. DPLGI), soybean (*Glycine max* var. Williams), field corn (*Zea mays* var. Pioneer 3732), wheat (*Triticum aestivium* var. Wheaton), rice (*Oryza sativa* var. Labelle), morningglory (*Ipomea lacumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum halepense*).

Preparation of Flats

Preemergence

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| | Herbicide Rating System | | |
|---|---|---|---|
| Rating Percent Control | Description of Main Categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |

Herbicide Rating System (continued)

| Rating Percent Control | Description of Main Categories | Crop Description | Weed Description |
| --- | --- | --- | --- |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss. | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | | % by Wt. |
| --- | --- | --- |
| Active ingredient | | 40.00 |
| Sodium lignosulfonate | | 20.00 |
| Attapulgite clay | | 40.00 |
| | Total | 100.00 |
| Active ingredient | | 90.00 |
| Dioctyl sodium sulfosuccinate | | 0.10 |
| Synthetic fine silica | | 9.90 |
| | Total | 100.00 |
| Active ingredient | | 20.00 |
| Sodium alkylnaphthalenesulfonate | | 4.00 |
| Sodium lignosulfonate | | 4.00 |
| Low viscosity methyl cellulose | | 3.00 |
| Attapulgite clay | | 69.00 |
| | Total | 100.00 |
| Active ingredient | | 25.00 |
| Base: | | 75.00 |
| 96% hydrated aluminum magnesium silicate 2% powdered sodium lignosulfonate 2% powdered anionic sodium alkylnaphthalenesulfonate | | |
| | Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | | % by Wt. |
| --- | --- | --- |
| Active ingredient | | 53.01 |
| Blend of alkylnaphthalenesulfonate and polyoxyethylene ethers | | 6.00 |
| Epoxidized soybean oil | | 1.00 |
| Xylene | | 39.99 |
| | Total | 100.00 |
| Active ingredient | | 10.00 |
| Blend of alkylnaphthalenesulfonate and polyoxyethylene ethers | | 4.00 |
| Xylene | | 86.00 |
| | Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | | % by Wt. |
|---|---|---|
| Active ingredient | | 46.00 |
| Colloidal magnesium aluminum silicate | | 0.40 |
| Sodium alkylnaphthalenesulfonate | | 2.00 |
| Paraformaldehyde | | 0.10 |
| Water | | 40.70 |
| Propylene glycol | | 7.50 |
| Acetylenic alcohols | | 2.50 |
| Xanthan gum | | 0.80 |
| | Total | 100.00 |
| Active ingredient | | 45.00 |
| Water | | 48.50 |
| Purified smectite clay | | 2.00 |
| Xanthan gum | | 0.50 |
| Sodium alkylnaphthalenesulfonate | | 1.00 |
| Acetylenic alcohols | | 3.00 |
| | Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively nonvolatile solvent such as water, corn oil, kerosene, propylene glycol, or other suitable solvents. The following illustrate specific suspensions:

| | | % by Wt. |
|---|---|---|
| Oil Suspension: | | |
| Active ingredient | | 25.00 |
| Polyoxyethylene sorbitol hexaoleate | | 5.00 |
| Highly aliphatic hydrocarbon oil | | 70.00 |
| | Total | 100.00 |
| Aqueous Suspension: | | |
| Active ingredient | | 40.00 |
| Polyacrylic acid thickener | | 0.30 |
| Dodecylphenol polyethylene glycol ether | | 0.50 |
| Disodium phosphate | | 1.00 |
| Monosodium phosphate | | 0.50 |
| Polyvinyl alcohol | | 1.00 |
| Water | | 56.70 |
| | Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxy-methyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)-glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethyl-amino)-1,3,5-triazin-2-yl]amino-2-methylpropanenitrile (cyanazine); dinitroaniline herbicides such as 2,6-dinitro-N,N-dipropyl-4-(trifluoromethyl)benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluo-meturon); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

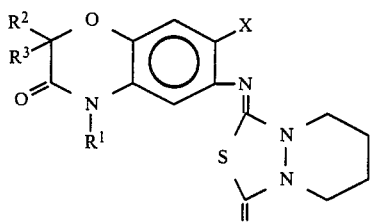

"W" is S

| Cmpd. No. | X | R¹ | R² | R³ |
|---|---|---|---|---|
| 1 | F | H | H | H |
| 2 | H | H | H | H |
| 3 | F | $CH_3$ | H | H |
| 4 | F | $C_2H_5$ | H | H |
| 5 | F | $CH_2CH_2CH_3$ | H | H |
| 6 | F | $CH_2C\equiv CH$ | H | H |
| 7 | F | $CH_2OCH_3$ | H | H |
| 8 | F | $CH_2SCH_3$ | H | H |
| 9 | F | $CH_2C_6H_5$ | H | H |
| 10 | Br | $CH_2C\equiv CH$ | H | H |
| 11 | F | $CH_2CH=CH_2$ | H | H |
| 12 | F | $CH_2OC_2H_5$ | H | H |
| 13 | Cl | $CH_2C\equiv CH$ | H | H |
| 14 | F | $CH_2C\equiv C-CH_3$ | H | H |
| 15 | F | $CH(CH_3)_2$ | H | H |
| 16 | F | $CH_2F$ | H | H |
| 17 | F | $CH_2CH_2F$ | H | H |
| 18 | F | $CH_2CN$ | H | H |
| 19 | F | $CH_2CH_2CH_2F$ | H | H |
| 20 | F | $CH_2CH_2CN$ | H | H |
| 21 | F | $CH_2CH=CH-CH_3$ | H | H |
| 22 | F | $CH(CH_3)CH_2CH_3$ | H | H |
| 23 | F | $CH_2CH(CH_3)CH_2CH_3$ | H | H |
| 24 | F | $OCH_3$ | H | H |
| 25 | F | $OCH_2CH_3$ | H | H |
| 26 | F | $CH_2SCH_2CH_3$ | H | H |
| 27 | F | $CH_2C(CH_3)=CH_2$ | H | H |
| 28 | F | $CH_2CH_2CH(CH_3)_2$ | H | H |
| 29 | F | $CH_2(CH_2)_3CH_3$ | H | H |
| 30 | F | $CH_2C\equiv CI$ | H | H |
| 31 | F | $CH_2(CH_2)_2CH_3$ | H | H |
| 32 | F | $CH_2$—cyclopropyl | H | H |
| 33 | F | $CH_2C(Cl)=CHCl$ (trans) | H | H |
| 34 | F | $CH_2C(Cl)=CHCl$ (cis) | H | H |
| 35 | F | $CH_2C(Br)=CH_2$ | H | H |
| 36 | F | $CH_2C(Cl)=CH_2$ | H | H |
| 37 | F | H | $CH_3$ | H |

TABLE 1-continued

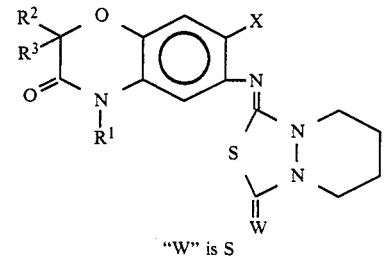

"W" is S

| Cmpd. No. | X | R¹ | R² | R³ |
|---|---|---|---|---|
| 38 | F | $CH_2C\equiv CH$ | $CH_3$ | H |
| 39 | F | $CH_2CH(CH_3)_2$ | H | H |
| 40 | H | $CH_2CH_2CH_3$ | H | H |
| 41 | F | cyclopropyl | H | H |

Other representative compounds are identical with Compounds 1–36 and 39–41 except that R² is methyl. Still others are identical with Compounds 1–41 except that W is oxygen.

I claim:

1. An herbicidal compound of the formula

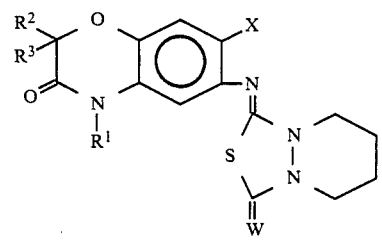

in which R¹ is hydrogen, alkyl, alkenyl, alkynyl, haloalkyl, haloalkenyl, haloalkynyl, alkoxyalkyl, alkoxyalkoxyalkyl, cycloalkyl, aralkyl, alkylthioalkyl, hydroxy, or alkoxy;

R² and R³ are independently hydrogen or alkyl;

X is hydrogen, chlorine, bromine, or fluorine; and

W is oxygen or sulfur.

2. The herbicidal compound of claim 1 in which W is sulfur.

3. The herbicidal compound of claim 1 in which each of R² and R³ is hydrogen.

4. The herbicidal compound of claim 1 in which X is fluorine.

5. The herbicidal compound of claim 1 in which W is sulfur, each of R² and R³ is hydrogen, and X is fluorine.

6. An herbicidal composition comprising an herbicidally effective amount of a compound of claim 1 in admixture with an agriculturally acceptable carrier.

7. A method for controlling undesired plant growth which comprises applying to the locus where control is desired an herbicidally effective amount of the composition of claim 6.

* * * * *